United States Patent
Yokoi et al.

(10) Patent No.: US 10,647,653 B2
(45) Date of Patent: May 12, 2020

(54) CRYSTAL OF MONOVALENT CATION SALT OF 3-HYDROXYISOVALERIC ACID AND PROCESS FOR PRODUCING THE CRYSTAL

(71) Applicants: KYOWA HAKKO BIO CO., LTD., Tokyo (JP); OTSUKA PHARMACEUTICAL FACTORY, INC., Naruto-shi (JP)

(72) Inventors: Tomoya Yokoi, Tokyo (JP); Hiroshi Nagano, Tokyo (JP); Takayuki Shimizu, Naruto (JP)

(73) Assignees: KYOWA HAKKO BIO CO., LTD., Tokyo (JP); OTSUKA PHARMACEUTICAL FACTORY, INC., Naruto (JP)

( * ) Notice: Subject to any disclaimer, the term of this patent is extended or adjusted under 35 U.S.C. 154(b) by 0 days.

(21) Appl. No.: 15/777,318

(22) PCT Filed: Nov. 18, 2016

(86) PCT No.: PCT/JP2016/084288
§ 371 (c)(1),
(2) Date: May 18, 2018

(87) PCT Pub. No.: WO2017/086447
PCT Pub. Date: May 26, 2017

(65) Prior Publication Data
US 2018/0327344 A1    Nov. 15, 2018

(30) Foreign Application Priority Data

Nov. 19, 2015  (JP) ................. 2015-226876
May 31, 2016   (JP) ................. 2016-108805

(51) Int. Cl.
| | | |
|---|---|---|
| C07C 59/01 | (2006.01) | |
| C07C 51/43 | (2006.01) | |
| C30B 7/10  | (2006.01) | |
| C30B 29/58 | (2006.01) | |

(52) U.S. Cl.
CPC ............. *C07C 59/01* (2013.01); *C07C 51/43* (2013.01); *C30B 7/105* (2013.01); *C30B 29/58* (2013.01); *C07B 2200/13* (2013.01)

(58) Field of Classification Search
None
See application file for complete search history.

(56) References Cited

U.S. PATENT DOCUMENTS

| | | | |
|---|---|---|---|
| 4,579,955 | A  | 4/1986  | Lammerant et al. |
| 5,360,613 | A  | 11/1994 | Nissen |
| 6,031,000 | A  | 2/2000  | Nissen et al. |
| 6,248,922 | B1 | 6/2001  | McCoy et al. |
| 9,598,344 | B2 | 3/2017  | Long et al. |
| 2004/0143136 | A1 | 7/2004 | Heyl-Frank et al. |
| 2004/0176449 | A1 | 9/2004 | Abraham et al. |
| 2013/0012565 | A1 | 1/2013 | Tung et al. |
| 2014/0256980 | A1 | 9/2014 | Li |
| 2019/0210958 | A1 | 7/2019 | Yokoi et al. |

FOREIGN PATENT DOCUMENTS

| | | |
|---|---|---|
| CN | 1434025 A       | 8/2003 |
| JP | S57-128653 A    | 8/1982 |
| JP | S58-201746 A    | 11/1983 |
| JP | H08-501777 A    | 2/1996 |
| JP | 2002-518440 A   | 6/2002 |
| JP | 2014-513046 A   | 5/2014 |
| WO | WO 2013/025775 A1 | 2/2013 |
| WO | WO 2014/166273 A1 | 10/2014 |
| WO | WO 2017/222043 A1 | 12/2017 |

OTHER PUBLICATIONS

Michaëlsson et al., "Long term calcium intake and rates of all cause and cardiovascular mortality: community based prospective longitudinal cohort study," *BMJ*, 346: f228 (2013).
Sharp et al., "Effect of leucine metabolite β-hydroxy-β-methylbutyrate on muscle metabolism during resistance-exercise training," *J. Appl. Physiol.*, 81(5): 2095-2104 (1996).
The Chemical Society of Japan, 4th Edition Jikken Kagaku Koa 1 Kihon Sosa I, pp. 184-186 (Maruzen Co., Ltd., 1990).
Wilson et al., "Effects of beta-hydroxy-beta-methylbutyrate (HMB) on exercise performance and body composition across varying levels of age, sex, and training experience: A review," *Nutr. Metab. (Lond,)*, 5: 1 (2008).
Wilson et al., "International Society of Sports Nutrition Position Stand: beta-hydroxy-beta-methylbutyrate (HMB)," *J. Int. Soc. Sports Nutr.*, 10(1): 6 (2013).
Japanese Patent Office, International Search Report in International Patent Application No. PCT/JP2016/084288 (dated Jan. 10, 2017).
European Patent Office, Extended European Search Report in European Patent Application No. 16866447.2 (dated May 9, 2019).
Nissen et al., "Effect of leucine metabolite β-hydroxy-η-methylbutyrate on muscle metabolism during resistance-exercise training," *J. Appl. Physiol.*, 81(5): 2095-2104 (1996).
Japanese Patent Office, International Search Report in International Patent Application No. PCT/JP2017/023174 (dated Sep. 19, 2017).
Japanese Patent Office, International Preliminary Report on Patentability in International Patent Application No. PCT/JP2017/023174 (dated Dec. 25, 2018).
Japanese Patent Office, International Preliminary Report on Patentability in Japanese Patent Application No. PCT/JP2016/084288 (dated May 22, 2018).

*Primary Examiner* — Ana Z Muresan
(74) *Attorney, Agent, or Firm* — Leydig, Voit & Mayer, Ltd.

(57) ABSTRACT

The present invention provides a crystal of a monovalent cation salt of 3-hydroxyisovaleric acid (hereinafter, referred to as HMB), which is excellent in solubility and easy to handle, and a process for producing the crystal. A crystal of a monovalent cation salt of HMB is precipitated in an aqueous HMB solution containing a monovalent cation-containing compound and having a pH of 4.0 to 9.0, and the crystal of a monovalent cation salt of HMB is thereafter collected from the aqueous solution.

23 Claims, 10 Drawing Sheets

CRYSTAL OF MONOVALENT CATION SALT OF 3-HYDROXYISOVALERIC ACID AND PROCESS FOR PRODUCING THE CRYSTAL

CROSS-REFERENCE TO RELATED APPLICATIONS

This patent application is the U.S. national phase of International Patent Application No. PCT/JP2016/084288, filed Nov. 18, 2016, which claims the benefit of Japanese Patent Application No. 2015-226876, filed on Nov. 19, 2015, and Japanese Patent Application No. 2016-108805, filed on May 31, 2016 which are incorporated by reference in their entireties herein.

TECHNICAL FIELD

The present invention relates to a crystal of a monovalent cation salt of 3-hydroxyisovaleric acid (β-hydroxy-β-methylbutyrate) (hereinafter, referred to as HMB) which is useful, for example, as a product, a raw material, an intermediate or the like of health food, medicines, cosmetics, or the like, and a process for producing the crystal.

BACKGROUND ART

HMB is useful, for example, as a product, a raw material, an intermediate or the like of health food, pharmaceutical preparations, cosmetics, or the like. HMB is an organic acid obtained by leucine metabolism in the body and is supposed to have an efficacy in building of muscle or preventing degradation of muscle (Non-Patent Documents 1 and 2).

From a commercial perspective, HMB is distributed in the market only in the form of either a free carboxylic acid or a Ca salt. Particularly, in supplement/health food applications, a Ca salt is used in most cases, because the Ca salt is a powder and excellent in handling (Non-Patent Document 3).

Ca is an important mineral playing a role in the bone formation, nerve activity, muscle movement, and the like. However, it has been recently reported that a Ca overdose leads to an increased risk of death due to cardiovascular disease or ischemic heart disease (Non-Patent Document 4).

RELATED ART

Patent Document

Patent Document 1: WO 2014/166273
Patent Document 2: U.S. Pat. No. 6,248,922
Patent Document 3: WO 2013/025775

Non-Patent Document

Non-Patent Document 1: Journal of Applied Physiology, Vol. 81, p. 2095, 1996
Non-Patent Document 2: Nutrition & Metabolism, Vol. 5, p. 1, 2008
Non-Patent Document 3: Journal of the International Society of Sports Nutrition, Vol. 10, p. 6, 2013
Non-Patent Document 4: The BMJ., Vol. 346, p. 228, 2013

DISCLOSURE OF INVENTION

Problems to be Solved by the Invention

In the pharmaceutical preparation field, there is a problem that Ca derived from a Ca salt readily binds to another component such as phosphate to form an insoluble salt and a high-concentration solution cannot be prepared. As to a Ca salt (Patent Documents 1 to 3) and a Mg salt (Patent Document 1), a production process utilizing crystallization is disclosed but, on the other hand, in regard to the salt form except for Ca and Mg, there is not a known crystal for any salt forms, and an industrially useful crystal of an HMB salt and a production process thereof are demanded.

Accordingly, an object of the present invention is to provide a crystal of a monovalent cation salt of HMB, which is excellent in solubility and easy to handle, and a production process thereof.

Means for Solving the Problems

The present invention relates to the following (1) to (23).
(1) A crystal of a monovalent cation salt of HMB.
(2) The crystal of (1) above, wherein the monovalent cation salt is a sodium salt.
(3) The crystal of (1) above, wherein the monovalent cation salt is a potassium salt.
(4) The crystal of (1) above, wherein the monovalent cation salt is an ammonium salt.
(5) The crystal of (2) above, wherein in powder X-ray diffraction, the crystal has peaks at diffraction angles (2θ) of 8.4±0.2°, 6.6±0.2°, 19.7±0.20, 13.3±0.2°, and 29.4±0.2°.
(6) The crystal of (5) above, wherein in powder X-ray diffraction, the crystal further has peaks at diffraction angles (2θ) of 35.1±0.2°, 17.3±0.2, 24.5±0.2°, 17.8±0.2°, and 29.9±0.2°.
(7) The crystal of (6) above, wherein in powder X-ray diffraction, the crystal further has peaks at diffraction angles (2θ) of 16.6±0.2°, 23.9±0.2°, 18.8±0.20, 18.0±0.2°, and 25.3±0.2°.
(8) The crystal of (2) above, wherein in powder X-ray diffraction, the crystal has peaks at diffraction angles (2θ) of 6.7±0.2°, 13.3±0.2°, and 20.0±0.2°.
(9) The crystal of (8) above, wherein in powder X-ray diffraction, the crystal further has peaks at diffraction angles (2θ) of 6.0±0.2°, 47.7±0.2°, 40.6±0.2°, 26.7±0.2°, and 12.0±0.20.
(10) The crystal of (8) or (9) above, wherein the crystal has approximately the following unit cell parameters when measured at about −180° C.: a=10.6679 Å; b=5.8862 Å; c=26.736 Å; α=90°; β97.966°; γ=90°; V=1662.6 Å$^3$; and Z=8; the calculated density ($D_{calc}$, gcm$^{-3}$) is 1.407 gcm$^{-3}$; and the space group is C2/c.
(11) The crystal of (3) above, wherein in powder X-ray diffraction, the crystal has peaks at diffraction angles (2θ) of 9.0±0.2°, 27.1±0.2°, 23.8±0.2°, 16.1±0.2°, and 22.9±0.2°.
(12) The crystal of (11) above, wherein in powder X-ray diffraction, the crystal further has peaks at diffraction angles (2θ) of 30.7±0.20, 8.1±0.20, 6.4±0.2°, 32.1±0.2°, and 28.5±0.20.
(13) The crystal of (12) above, wherein in powder X-ray diffraction, the crystal further has peaks at diffraction angles (2θ) of 40.1±0.20, 31.1±0.2°, 24.6±0.2°, 18.7±0.2°, and 34.4±0.2°.
(14) The crystal of (4) above, wherein in powder X-ray diffraction, the crystal has peaks at diffraction angles (2θ) of 19.9±0.2°, 21.1±0.2°, 29.9±0.2°, 17.3±0.2°, and 18.00.2°.
(15) The crystal of (14) above, wherein in powder X-ray diffraction, the crystal further has peaks at diffraction angles (2θ) of 25.6±0.2°, 8.6±0.2°, 18.2±0.2°, 39.6±0.2°, and 40.5±0.20.

(16) The crystal of (15) above, wherein in powder X-ray diffraction, the crystal further has peaks at diffraction angles (2θ) of 28.8±0.2°, 39.7±0.2°, 18.6±0.20, 15.5±0.2°, and 14.3±0.20.

(17) A process for producing a crystal of a monovalent cation salt of HMB, comprising a step of concentrating an aqueous HMB solution containing a monovalent cation-containing compound and having a pH of 4.0 to 10.0 under reduced pressure at 20 to 60° C. to precipitate a crystal of a monovalent cation salt of HMB in the aqueous solution, and a step of collecting the crystal of a monovalent cation salt of HMB from the aqueous solution.

(18) A process for producing a crystal of a monovalent cation salt of HMB, comprising a step of adding, as a seed crystal, a crystal of a monovalent cation salt of HMB to an aqueous HMB solution containing a monovalent cation-containing compound and having a pH of 4.0 to 10.0, a step of precipitating a crystal of a monovalent cation salt of HMB in the aqueous solution, and a step of collecting the crystal of a monovalent cation salt of HMB from the aqueous solution.

(19) The process of (18) above, wherein the step of precipitating a monovalent cation salt of HMB is a step of adding or adding dropwise a solvent selected from the group consisting of nitrile and ketone to precipitate a crystal of a monovalent cation salt of HMB.

(20) The process of (19) above, wherein the nitrile is acetonitrile and the ketone is a solvent selected from the group consisting of acetone, methyl ethyl ketone, methyl isobutyl ketone and diethyl ketone.

(21) The process of any one of (17) to (20) above, wherein the monovalent cation-containing compound is a sodium-containing compound and the monovalent cation salt is a sodium salt.

(22) The process of any one of (17) to (20) above, wherein the monovalent cation-containing compound is a potassium-containing compound and the monovalent cation salt is a potassium salt.

(23) The process of any one of (17) to (20) above, wherein the monovalent cation-containing compound is an ammonium-containing compound and the monovalent cation salt is an ammonium salt.

Effects of the Invention

According to the present invention, a crystal of a monovalent cation salt of HMB, which is easy to handle, and a production process thereof are provided. The crystal of a monovalent cation salt of HMB of the present invention is a salt crystal having superiority such as exhibiting high solubility, not forming an insoluble salt, and not inducing electrolyte abnormality, as compared to a calcium salt.

EMBODIMENTS FOR CARRYING OUT THE INVENTION

1. Crystal of the Present Invention

Figure 1:
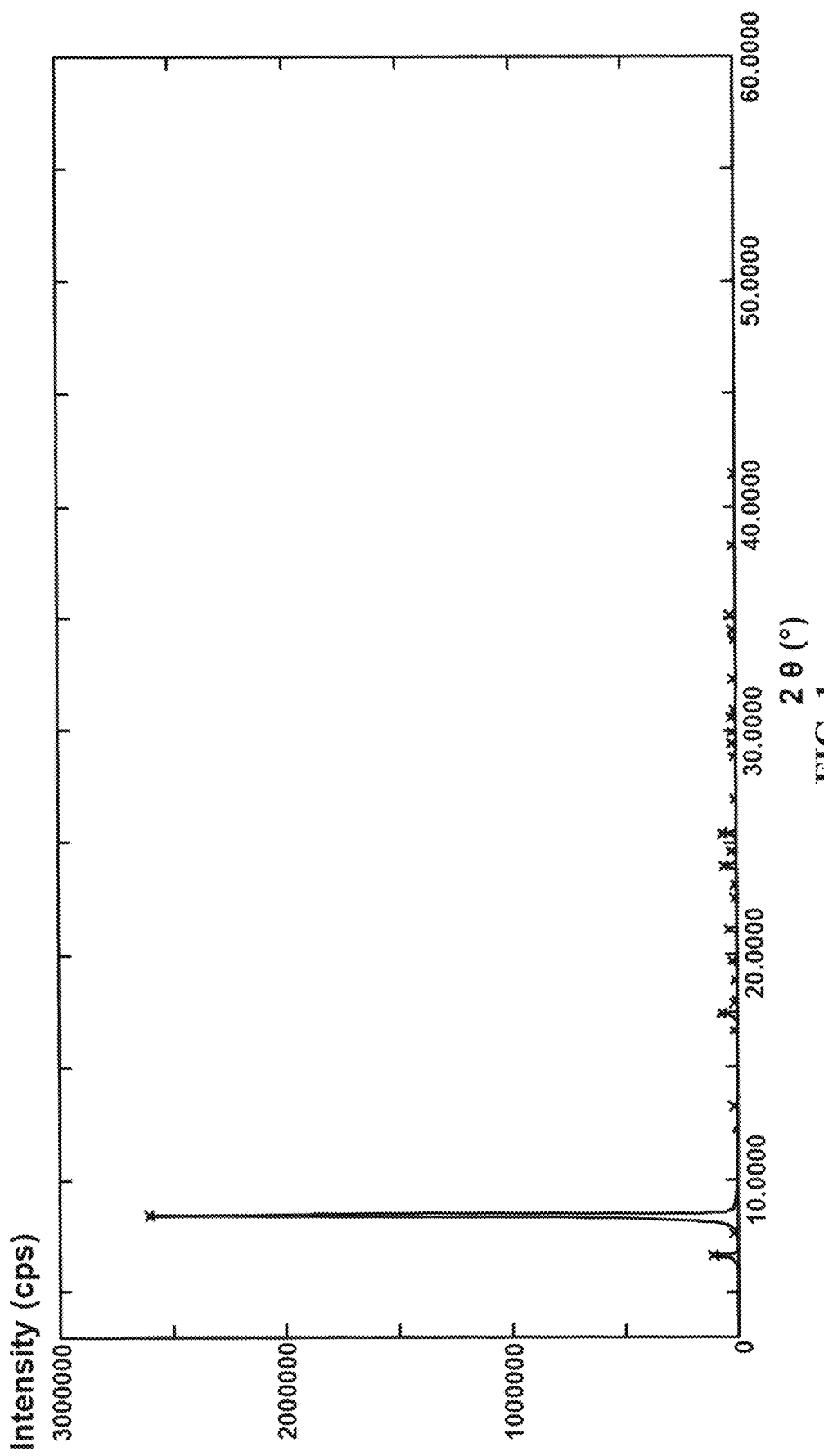
FIG. 1 illustrates the results of powder X-ray diffraction of the crystal of sodium HMB nonhydrate obtained in Example 1.

The crystal of the present invention is a crystal of a monovalent cation salt of HMB, more specifically, sodium HMB, potassium HMB, or ammonium HMB (hereinafter, sometimes referred as the "crystal of the present invention"). The crystal of the present invention can be confirmed to be a crystal of HMB by the method using HPLC described in Analysis Examples later.

The crystal of the present invention can be confirmed to be a crystal of a sodium salt by measuring the sodium content in the crystal by means of the atomic absorption photometer described in Analysis Examples later. For example, the crystal of the present invention can be confirmed to be a crystal of a monosodium salt by the fact that the sodium content in the crystal is usually 16.4±3.0 wt %, preferably 16.4±2.0 wt %, most preferably 16.4±1.0 wt %.

The crystal of the present invention can be confirmed to be a crystal of a potassium salt by measuring the potassium content in the crystal by means of the atomic absorption photometer described in Analysis Examples later. For example, the crystal of the present invention can be confirmed to be a crystal of a monopotassium salt by the fact that the potassium content in the crystal is usually 25.0±3.0 wt %, preferably 25.0±2.0 wt %, most preferably 25.0±1.0 wt %.

The crystal of the present invention can be confirmed to be a crystal of an ammonium salt by measuring the ammonium content in the crystal by means of HPLC described in Analysis Examples later. For example, the crystal of the present invention can be confirmed to be a crystal of a monoammonium salt by the fact that the ammonium content in the crystal is usually 13.3±3.0 wt %, preferably 13.3±2.0 wt %/o, most preferably 13.3±1.0 wt %.

The crystal of the present invention can be confirmed to be a crystal of a nonhydrate or a hydrate by measurement using the Karl-Fischer method described in Analysis Examples later. In particular, a crystal in which the water content measured by the method above is usually 1.5 wt % or less, preferably 1.3 wt % or less, most preferably 1.0 wt % or less, can be confirmed to be a crystal of a nonhydrate. The crystal of sodium HMB can be confirmed to be a dihydrate by the fact the water content measured by the method above is usually 20.5±5.0 wt %, preferably 20.5±3.0 wt %, most preferably 20.5±1.0 wt %.

Figure 3:
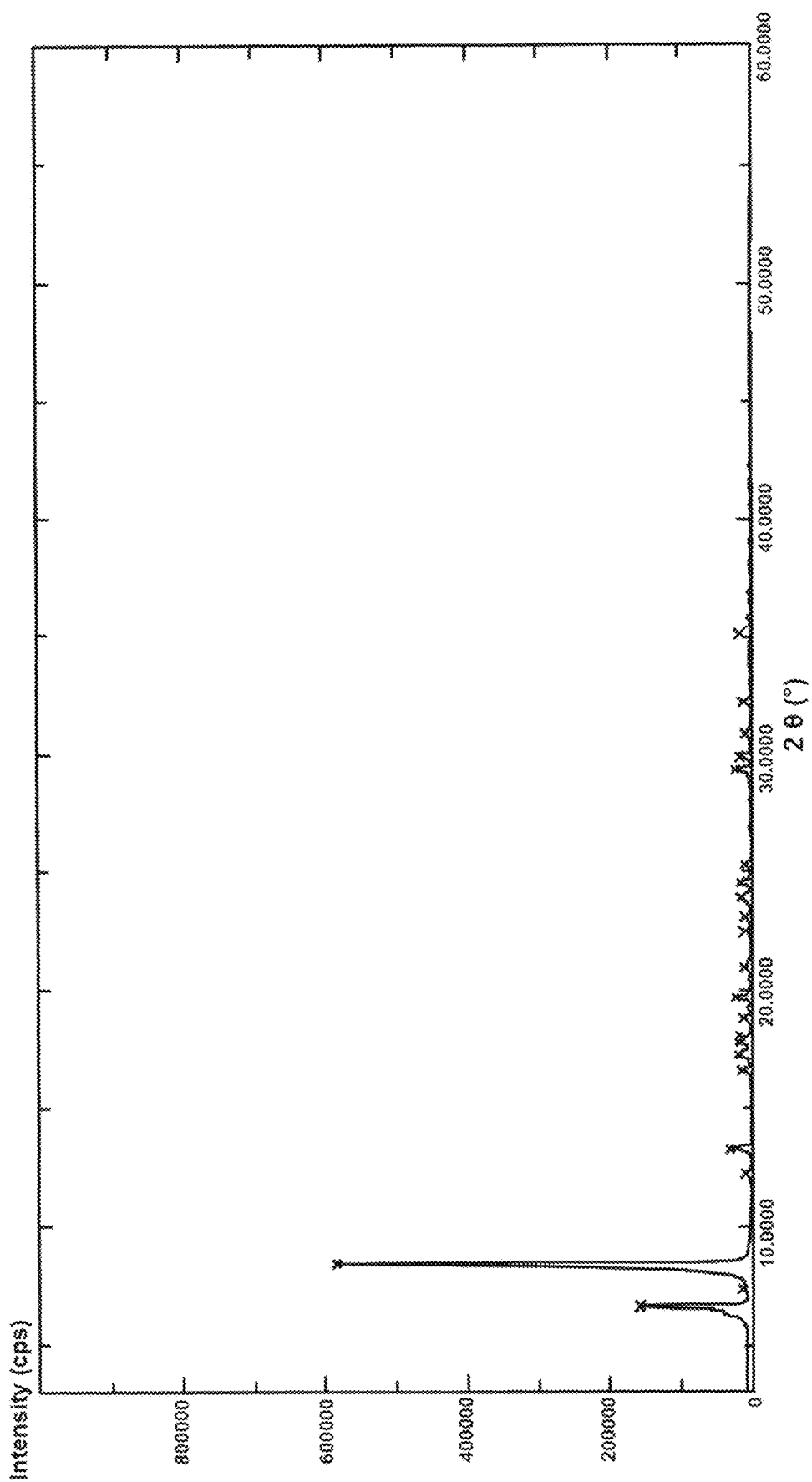
FIG. 3 illustrates the results of powder X-ray diffraction of the crystal of sodium HMB nonhydrate obtained in Example 2.

The crystal of sodium HMB nonhydrate includes a crystal of sodium HMB nonhydrate of which powder X-ray diffraction pattern using CuKα as the X-ray source is specified by the values shown in FIGS. 1 and 3 and Tables 1 and 3. Here, FIG. 1 and FIG. 3 correspond to the diffraction results of the crystal of sodium HMB nonhydrate of Table 1 and Table 3, respectively.

Figure 2:
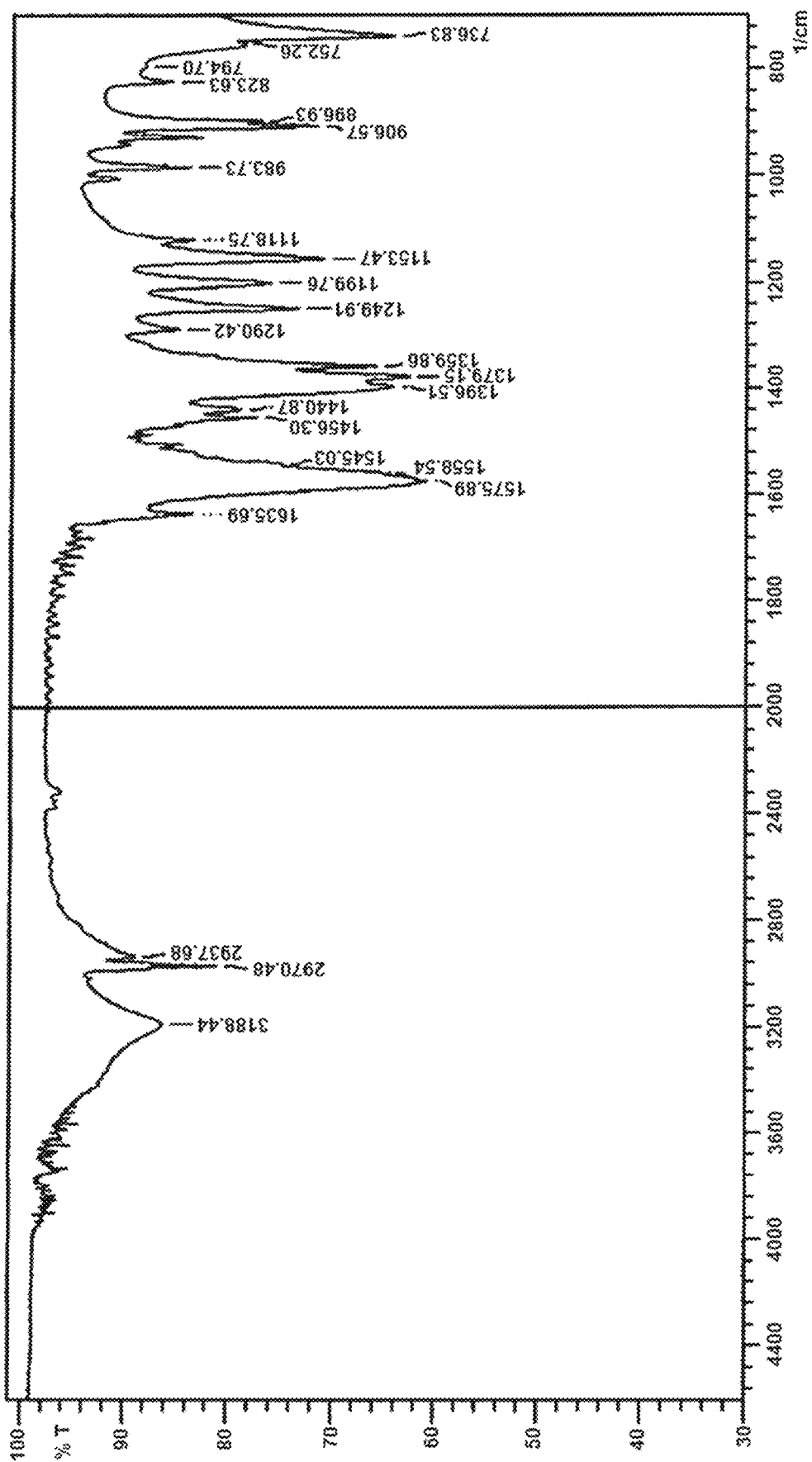
FIG. 2 illustrates the results of infrared spectroscopic (IR) analysis of the crystal of sodium HMB nonhydrate obtained in Example 1.
Figure 4:
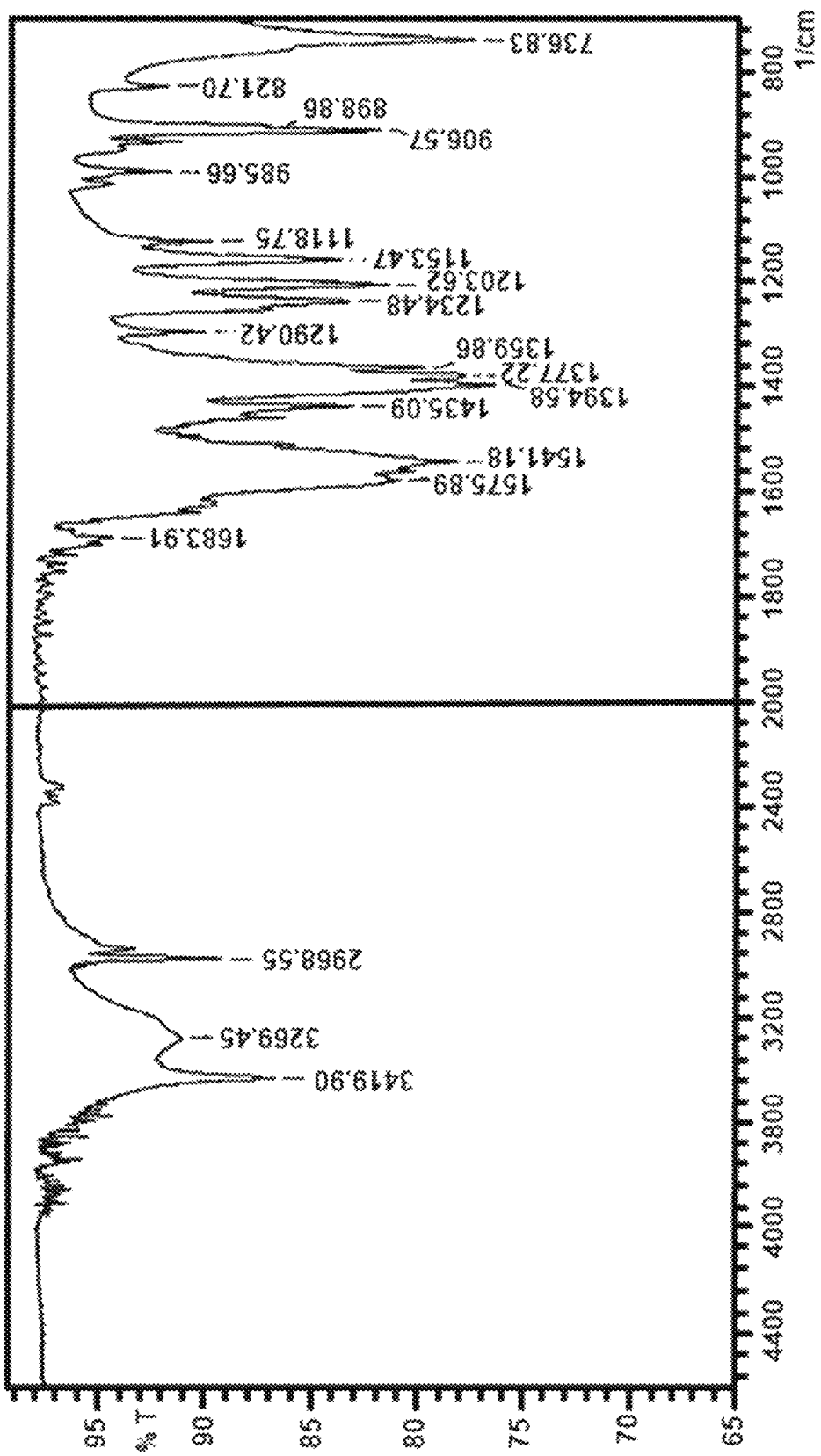
FIG. 4 illustrates the results of infrared spectroscopic (IR) analysis of the crystal of sodium HMB nonhydrate obtained in Example 2.

The crystal of sodium HMB nonhydrate also includes a crystal of sodium HMB nonhydrate which shows the infrared absorption spectrum illustrated in FIGS. 2 and 4 when subjected to the infrared (IR) analysis described in Analysis Examples later.

Specifically, the crystal of sodium HMB nonhydrate preferably has peaks at diffraction angles (2θ) of the following (i) in the powder X-ray diffraction using CuKα as the X-ray source, more preferably has peaks at diffraction angles (2θ) of the following (ii), in addition to the peaks at diffraction angles (2θ) of (i), still more preferably has peaks at diffraction angles (2θ) of the following (iii), in addition to the peaks at diffraction angles (2θ) of (i) and (ii):

(i) 8.4±0.2°, preferably 8.4±0.1; 6.6±0.2°, preferably 6.6±0.1°; 19.7±0.2°, preferably 19.7±0.1; 13.3±0.2°, preferably 13.3±0.1°; and 29.4±0.2°, preferably 29.4±0.1°, (ii) 35.1±0.2°, preferably 35.1±0.1°; 17.3±0.2°, preferably 17.3±0.1°; 24.5±0.2°, preferably 24.5±0.1°; 17.8±0.2°, preferably 17.8±0.1; and 29.9±0.2°, preferably 29.9±0.1°, (iii) 16.6±0.2°, preferably 16.6±0.1°; 23.9±0.2°, preferably 23.9±0.1°; 18.8±0.2°, preferably 18.8±0.1°; 18.0±0.2°, preferably 18.0±0.1°; and 25.3±0.2°, preferably 25.3±0.1°.

Figure 9:
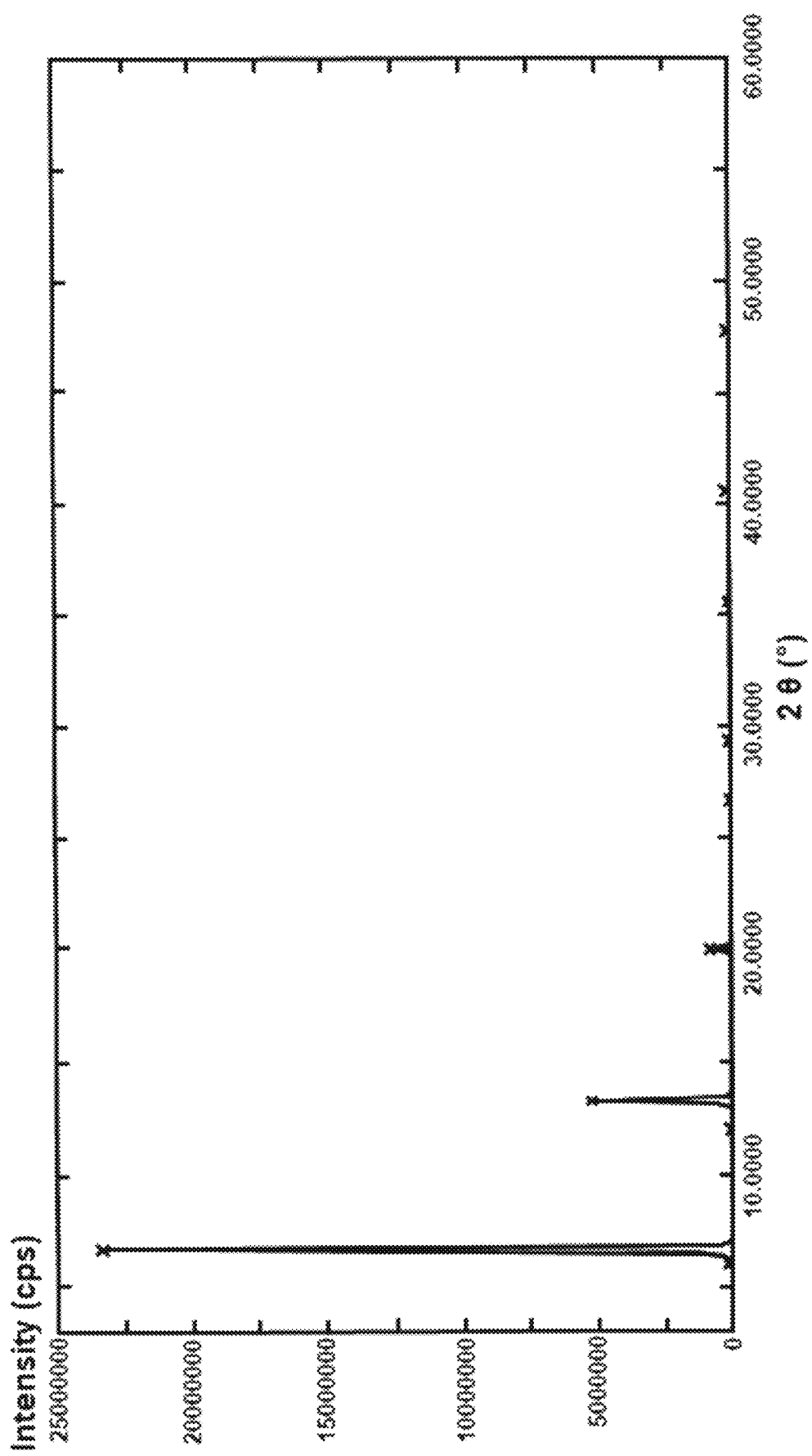
FIG. 9 illustrates the results of powder X-ray diffraction of the crystal of sodium HMB dihydrate obtained in Example 3.

The crystal of sodium HMB dihydrate includes a crystal of sodium HMB dihydrate of which powder X-ray diffraction pattern using CuKα as the X-ray source is specified by the values shown in FIG. 9 and Table 5.

Figure 10:
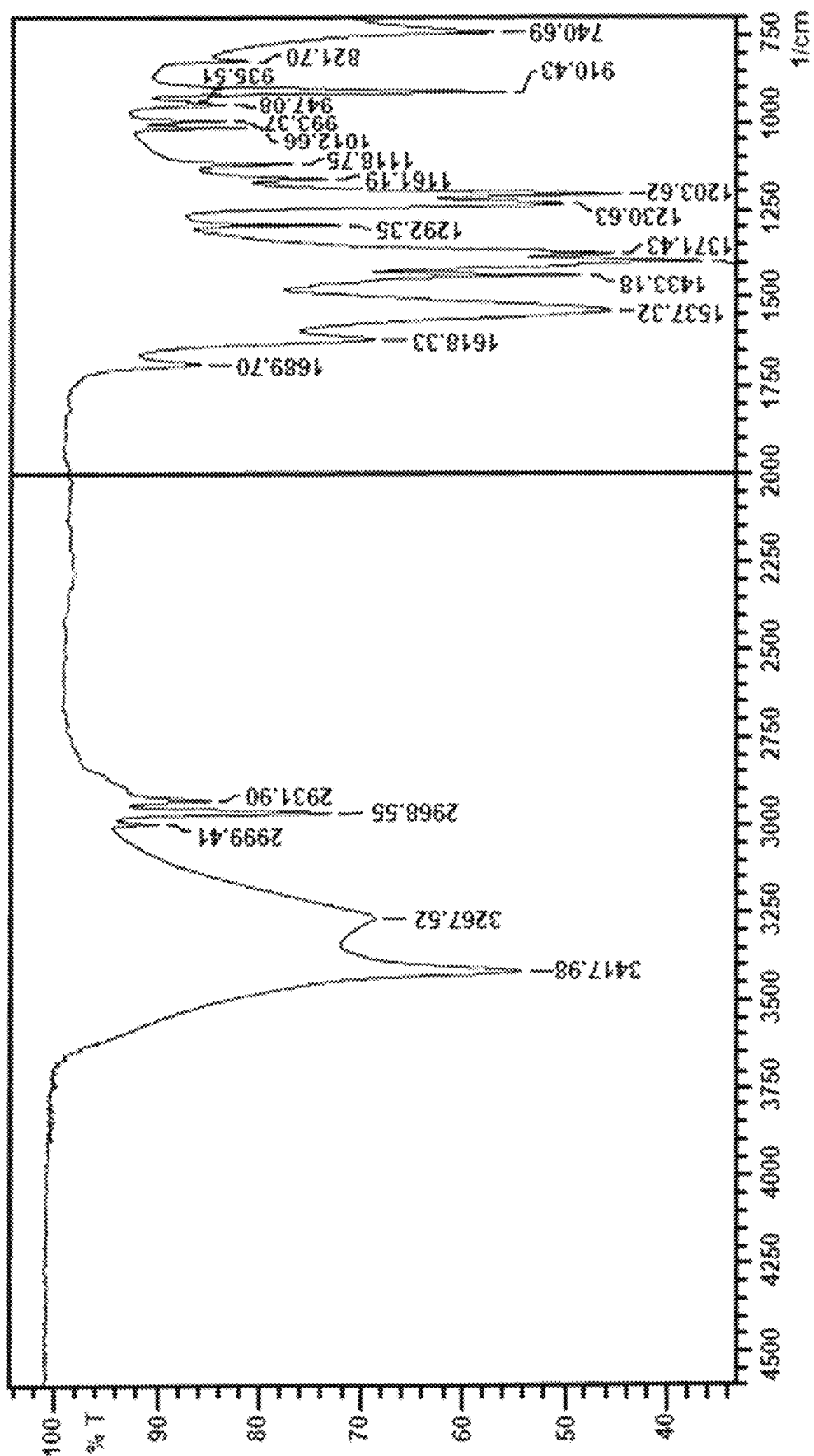
FIG. 10 illustrates the results of infrared spectroscopic (IR) analysis of the crystal of sodium HMB dihydrate obtained in Example 3.

The crystal of sodium HMB dihydrate also includes a crystal of sodium HMB dihydrate which shows the infrared absorption spectrum illustrated in FIG. 10 when subjected to the infrared (IR) analysis described in Analysis Examples later.

Specifically, the crystal of sodium HMB dihydrate preferably has peaks at diffraction angles (2θ) of the following (iv) in the powder X-ray diffraction using CuKα as the X-ray source, more preferably has peaks at diffraction angles (2θ) of the following (v), in addition to the peaks at diffraction angles (2θ) of (iv):

(iv) 6.7±0.2°, preferably 6.7±0.1°; 13.3±0.2°, preferably 13.3±0.1°; and 20.0±0.2°, preferably 20.0±0.10°,
(v) 6.0±0.2°, preferably 6.0±0.1; 47.7±0.2°, preferably 47.7±0.1°; 40.6±0.2°, preferably 40.6±0.1°; 26.7±0.2°, preferably 26.7±0.1°; and 12.0±0.2°, preferably 12.0±0.1°.

The method for determining the crystal structure includes structural analysis by a single crystal X-ray diffraction apparatus. A single crystal of a monovalent cation salt of HMB is fixed to the diffractometer, and the diffraction image is measured using an X-ray with a predetermined wavelength in the atmosphere at room temperature or in an inert gas stream at a predetermined temperature. Structure determination by a direct method and structure refinement by the least-square method are performed using a set of plane index and diffraction intensity calculated from the diffraction image, to obtain a single crystal structure.

In one embodiment, the crystalline form of sodium HMB dihydrate preferably shows single crystal X-ray crystallographic analysis results that the crystal has approximately the following parameters, i.e., unit lattice dimensions when measured at about −180° C.: a=10.6679 Å; b=5.8862 Å; c=26.736 Å; α=90°; β=97.966°; γ=900; V=1662.6 Å$^3$; and Z=8; the calculated density ($D_{calc}$, gcm$^{-3}$) is 1.407 gcm$^{-3}$; and the space group is C2/c. In one embodiment, the crystalline form of sodium HMB dihydrate is preferably represented by the formula: [Na$^+$.(C$_5$H$_9$O$_4$)$^-$.2H$_2$O].

Figure 5:
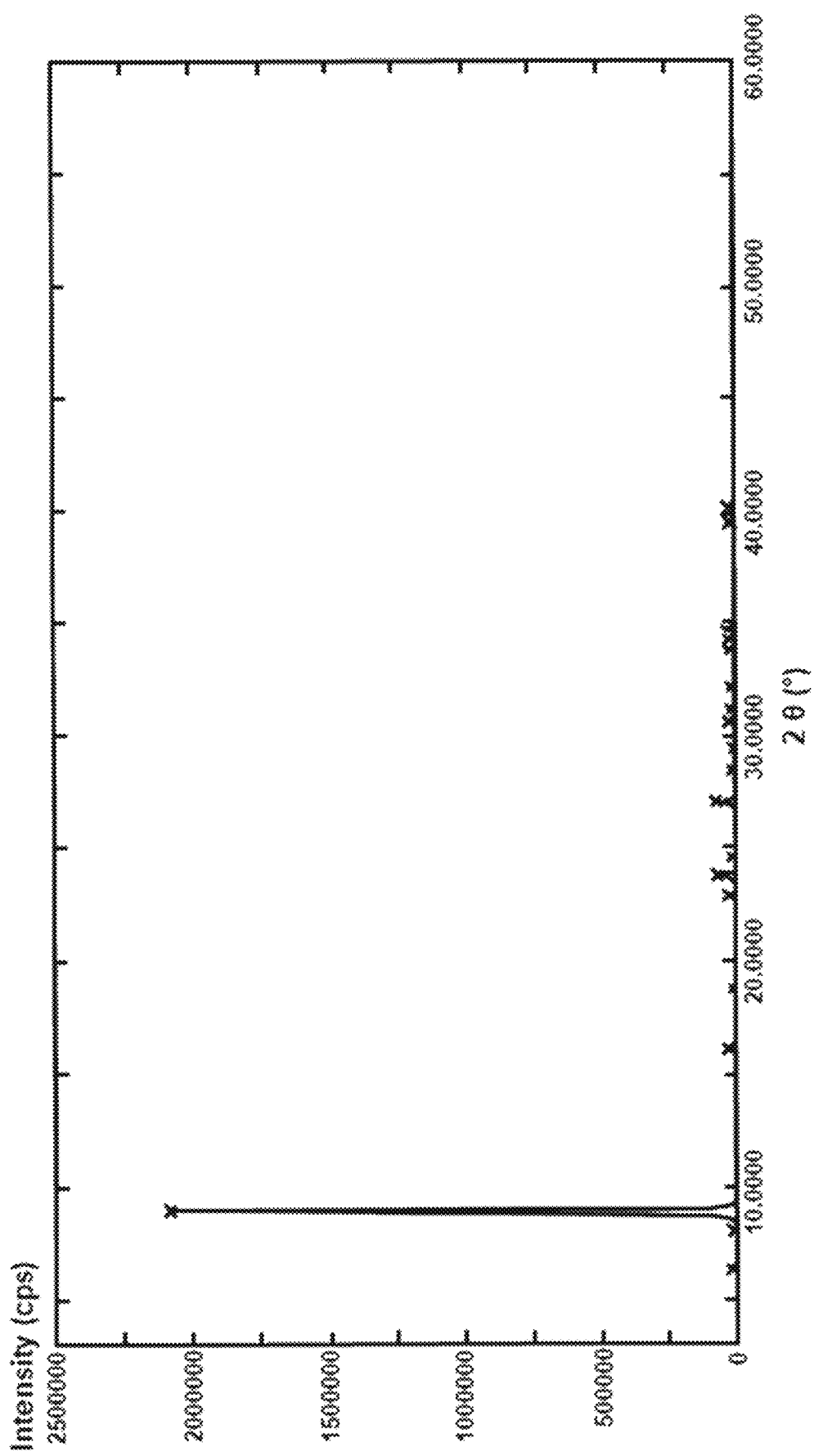
FIG. 5 illustrates the results of powder X-ray diffraction of the crystal of potassium HMB nonhydrate obtained in Example 5.

The crystal of potassium HMB nonhydrate includes a crystal of potassium HMB nonhydrate of which powder X-ray diffraction pattern using CuKα as the X-ray source is specified by the values shown in FIG. 5 and Table 8.

Figure 6:
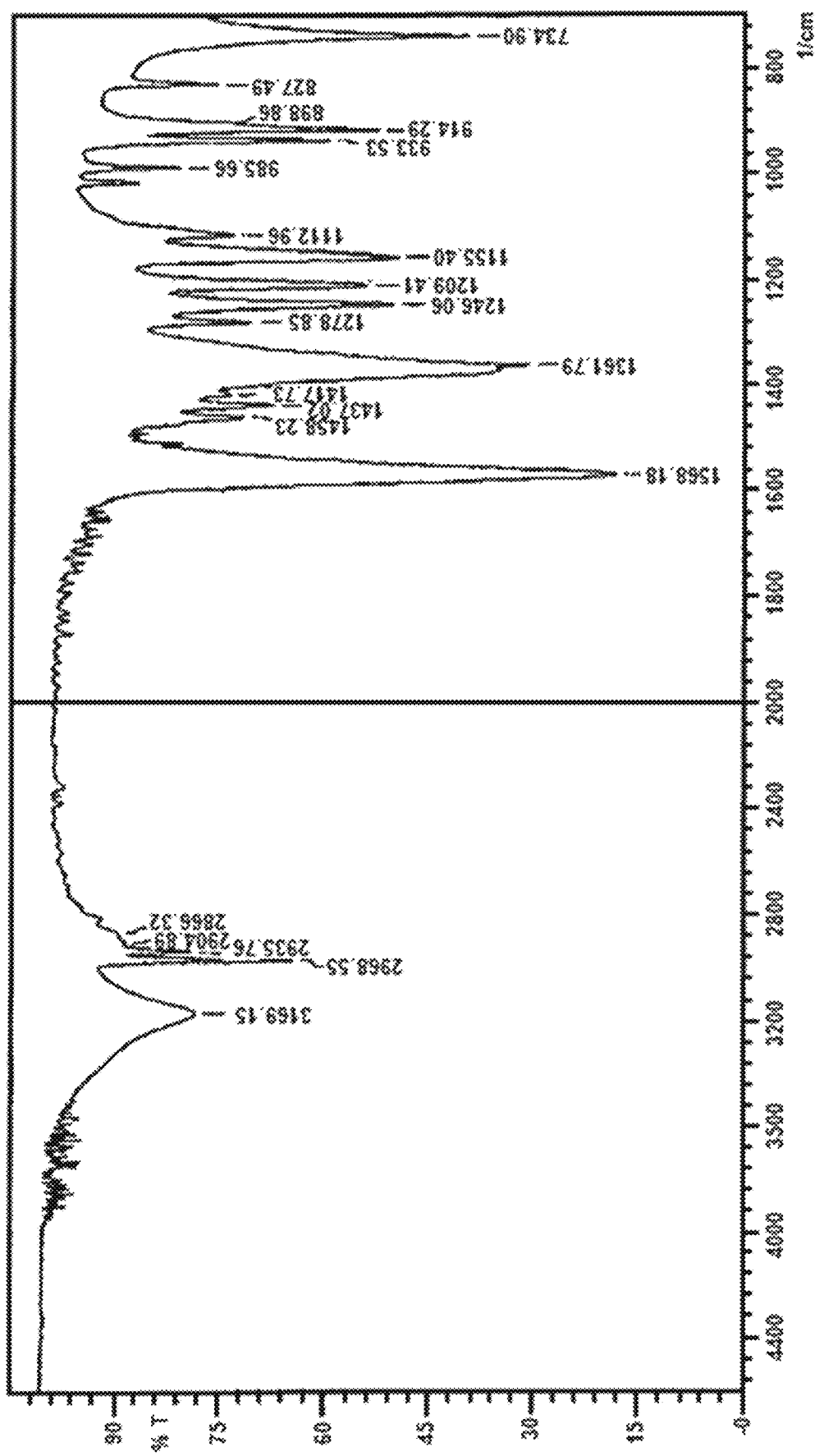
FIG. 6 illustrates the results of infrared spectroscopic (IR) analysis of the crystal of potassium HMB nonhydrate obtained in Example 5.

The crystal of potassium HMB nonhydrate also includes a crystal of potassium HMB nonhydrate which shows the infrared absorption spectrum illustrated in FIG. 6 when subjected to the infrared spectroscopic (IR) analysis described in Analysis Examples later.

Specifically, the crystal of potassium HMB nonhydrate preferably has peaks at diffraction angles (2θ) of the following (vi) in the powder X-ray diffraction using CuKα as the X-ray source, more preferably has peaks at diffraction angles (2θ) of the following (vii), in addition to the peaks at diffraction angles (2θ) of (vi), still more preferably has peaks at diffraction angles (2θ) of the following (viii), in addition to the peaks at diffraction angles (2θ) of (vi) and (vii):

(vi) 9.0±0.2°, preferably 9.0±0.1°; 27.1±0.2°, preferably 27.1±0.1°; 23.8±0.2°, preferably 23.8±0.1°; 16.1±0.2°, preferably 16.1±0.1°; and 22.9±0.2°, preferably 22.9±0.10,
(vii) 30.7±0.2°, preferably 30.7±0.1°; 8.1±0.2°, preferably 8.1±0.1°; 6.4±0.2°, preferably 6.4±0.1°; 32.1±0.2°, preferably 32.1±0.1°; and 28.5±0.2°, preferably 28.5±0.1°,
(viii) 40.1±0.2°, preferably 40.1±0.1°; 31.1±0.2°, preferably 31.1±0.1°; 24.6±0.2°, preferably 24.6±0.1; 18.7±0.2°, preferably 18.7±0.1°; and 34.4±0.2°, preferably 34.4±0.1.

Figure 7:
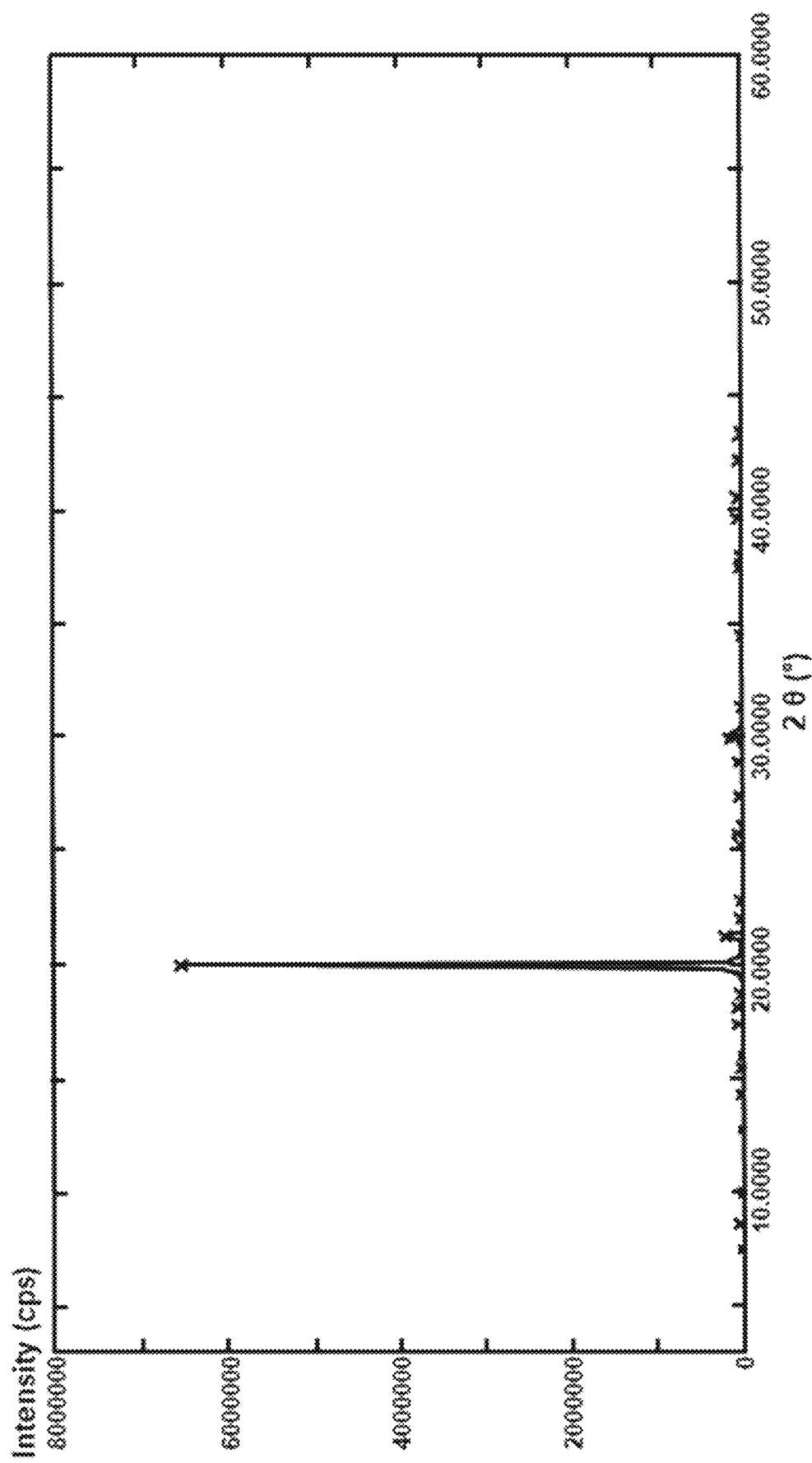
FIG. 7 illustrates the results of powder X-ray diffraction of the crystal of ammonium HMB nonhydrate obtained in Example 7.

The crystal of ammonium HMB nonhydrate includes a crystal of ammonium HMB nonhydrate of which powder X-ray diffraction pattern using CuKα as the X-ray source is specified by the values shown in FIG. 7 and Table 10.

Figure 8:
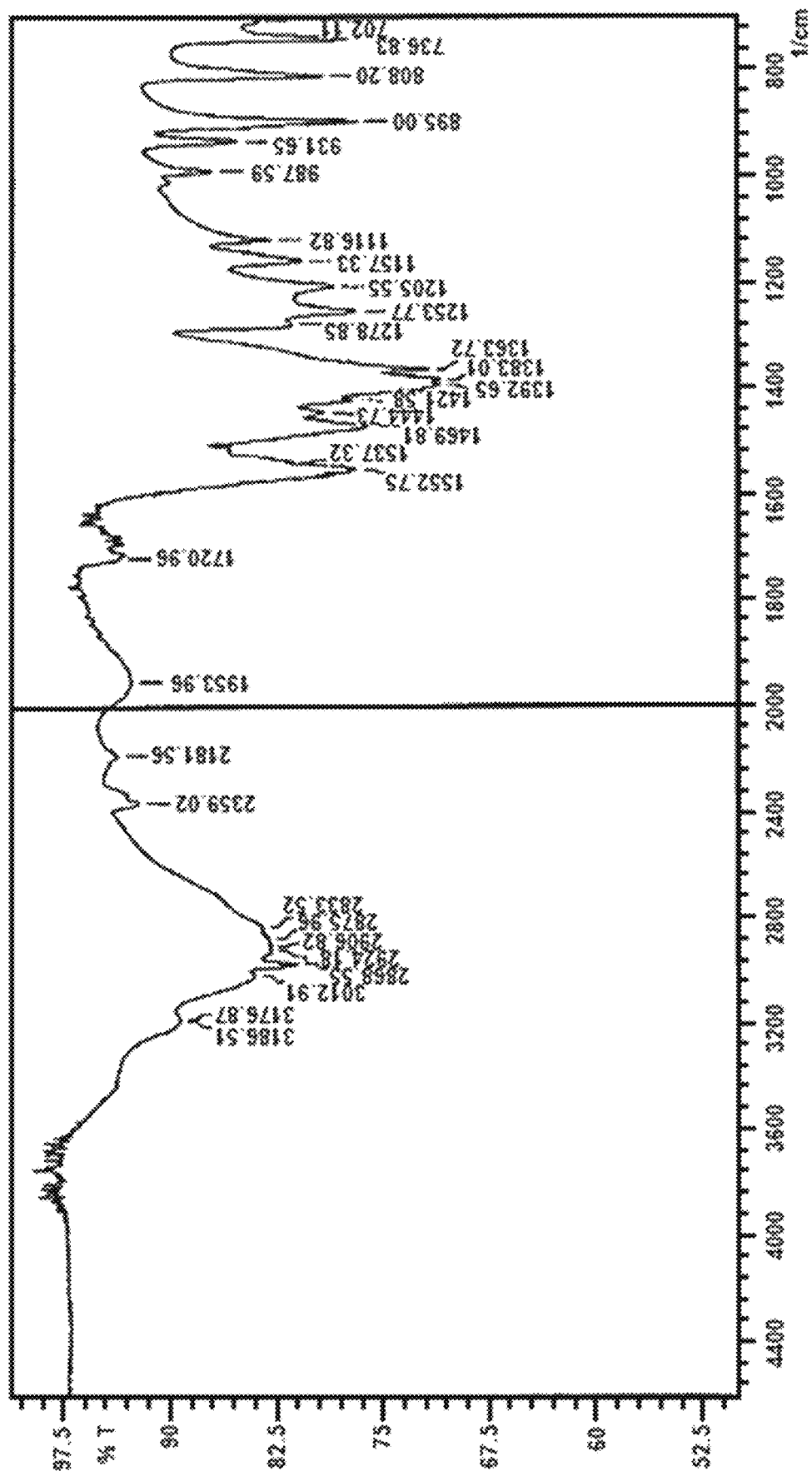
FIG. 8 illustrates the results of infrared spectroscopic (IR) analysis of the crystal of ammonium HMB nonhydrate obtained in Example 7.

The crystal of ammonium HMB nonhydrate also includes a crystal of ammonium HMB nonhydrate which shows the infrared absorption spectrum illustrated in FIG. 8 when subjected to the infrared spectroscopic (IR) analysis described in Analysis Examples later.

Specifically, the crystal of ammonium HMB nonhydrate preferably has peaks at diffraction angles (2θ) of the following (ix) in the powder X-ray diffraction using CuKα as the X-ray source, more preferably has peaks at diffraction angles (2θ) of the following (x), in addition to the peaks at diffraction angles (2θ) of (ix), still more preferably has peaks at diffraction angles (2θ) of the following (xi), in addition to the peaks at diffraction angles (2θ) of (ix) and (x):

(ix) 19.9±0.2°, preferably 19.9±0.1°; 21.1±0.2°, preferably 21.1±0.1; 29.9±0.2°, preferably 29.9±0.1°; 17.3±0.2°, preferably 17.3±0.1°; and 18.0±0.2°, preferably 18.0±0.10,
(x) 25.6±0.2°, preferably 25.6±0.1; 8.6±0.2°, preferably 8.6±0.1°; 18.2±0.2°, preferably 18.2±0.1°; 39.610.20, preferably 39.6±0.1°; and 40.5±0.2°, preferably 40.5±0.1°,
(xi) 28.8±0.2°, preferably 28.8±0.1°; 39.7±0.2°, preferably 39.7±0.1°; 18.6±0.2°, preferably 18.6±0.1°; 15.5±0.2°, preferably 15.5±0.1°; and 14.3±0.2°, preferably 14.3±0.1°.

2. Process for Producing Crystal of Monovalent Cation Salt of HMB of the Present Invention The process for producing the crystal of the present invention is the production process described below (hereinafter, sometimes referred to as the "crystal production process of the present invention").

The crystal production process of the present invention includes a process for producing a crystal of a monovalent cation salt of HMB, comprising a step of concentrating an aqueous HMB solution containing a monovalent cation-containing compound and having a pH of 4.0 to 10.0, more specifically, at least one compound selected from a sodium-containing compound, a potassium-containing compound and an ammonia-containing compound, at 20 to 60° C. to precipitate a crystal of a monovalent cation salt of HMB, more specifically, at least one crystal selected from a crystal of sodium HMB, a crystal of potassium HMB and a crystal of ammonium HMB, in the aqueous solution, and a step of collecting the crystal of a monovalent cation salt of HMB from the aqueous solution.

HMB contained in the aqueous HMB solution may be a compound produced by any production method such as fermentation method, enzyme method, extraction method from natural products, or chemical synthesis method.

In the case where a solid matter hindering the crystallization is contained in the aqueous HMB solution, the solid matter can be removed using centrifugal separation, filtration, ceramic filter, or the like. In the case where a water-soluble impurity or salt hindering the crystallization is contained in the aqueous HMB solution, the water-soluble impurity or salt can be removed, for example, by passing the aqueous solution through a column packed with an ion exchange resin, or the like.

In the case where a hydrophobic impurity hindering the crystallization is contained in the aqueous HMB solution, the hydrophobic impurity can be removed, for example, by passing the aqueous solution through a column packed with a synthetic adsorption resin, activated carbon, or the like. The aqueous solution may be prepared to have an HMB concentration of usually 500 g/L or more, preferably 600 g/L or more, more preferably 700 g/L or more, most preferably 800 g/L or more.

The sodium-containing compound includes, for example, a basic compound such as sodium hydroxide, or a neutral salt such as carbonated sodium, sulfated sodium, nitrated sodium or chlorinated sodium. The neutral salt includes, for example, sodium carbonate, sodium sulfate, sodium nitrate or sodium chloride.

In the case of using a basic compound as the sodium-containing compound, the pH of the aqueous HMB solution is adjusted using the basic compound, and an aqueous HMB solution containing a sodium-containing compound and having a pH of usually from 4.0 to 10.0, preferably from 4.5 to 9.5, most preferably from 5.0 to 9.0, can thereby be obtained.

The potassium-containing compound includes, for example, a basic compound such as potassium hydroxide, or a neutral salt such as carbonated potassium, sulfated potassium, nitrated potassium or chlorinated potassium. The neutral salt includes, for example, potassium carbonate, potassium sulfate, potassium nitrate or potassium chloride.

In the case of using a basic compound as the potassium-containing compound, the pH of the aqueous HMB solution is adjusted using the basic compound, and an aqueous HMB solution containing a potassium-containing compound and having a pH of usually from 4.0 to 10.0, preferably from 4.5 to 9.5, most preferably from 5.0 to 9.0, can thereby be obtained.

The ammonium-containing compound includes, for example, a basic compound such as aqueous ammonium solution, or a neutral salt such as carbonated ammonium, sulfated ammonium, nitrated ammonium or chlorinated ammonium. The neutral salt includes, for example, ammonium carbonate, ammonium sulfate, ammonium nitrate or ammonium chloride.

In the case of using a basic compound as the ammonium-containing compound, the pH of the aqueous HMB solution is adjusted using the basic compound, and an aqueous HMB solution containing an ammonium-containing compound and having a pH of usually from 4.0 to 10.0, preferably from 4.5 to 9.5, most preferably from 5.0 to 9.0, can thereby be obtained.

The process for precipitating a crystal of a monovalent cation salt of HMB in the aqueous solution above includes, for example, a process of concentrating the aqueous solution under reduced pressure, and a process of adding or adding dropwise a solvent selected from the group consisting of nitrile and ketone in the aqueous solution. Of these processes, one or more processes can be used in combination.

In the process of concentrating the aqueous solution under reduced pressure, the temperature of the aqueous solution is usually from 0 to 100° C., preferably from 10 to 90° C., most preferably from 20 to 60° C. In the process of concentrating the aqueous solution under reduced pressure, the pressure reduction time is usually from 1 to 120 hours, preferably from 2 to 60 hours, most preferably from 3 to 50 hours.

In the process of adding or adding dropwise a solvent selected from the group consisting of nitrile and ketone in the aqueous solution to precipitate a crystal of a monovalent cation salt of HMB, a crystal of a monovalent cation salt of HMB may be added as a seed crystal before or after starting addition of a solvent selected from the group consisting of nitrile and ketone but before precipitation of a crystal of a monovalent cation salt of HMB. The seed crystal includes a crystal of a monovalent cation salt of HMB produced by the process of concentrating the aqueous solution under reduced pressure.

The timing of adding the seed crystal may be any time as long as it is before the crystal of a monovalent cation salt of HMB is precipitated, but is usually within 0 to 5 hours, preferably within 0 to 4 hours, most preferably within 0 to 3 hours, after starting adding dropwise or adding a solvent selected from the group consisting of nitrile and ketone.

The nitrile is preferably acetonitrile, and the ketone is preferably ketone selected from the group consisting of acetone, methyl ethyl ketone, methyl isobutyl ketone and diethyl ketone, more preferably ketone selected from the group consisting of acetone and methyl ethyl ketone, still more preferably acetone.

At the time of adding or adding dropwise a solvent selected from the group consisting of nitrile and ketone, the temperature of the aqueous solution may be any temperature as long as it is a temperature not causing decomposition of HMB, but in order to enhance the crystallization ratio of the crystal of a monovalent cation salt of HMB by lowering the solubility, the temperature is usually 80° C. or less, preferably 70° C. or less, more preferably 60° C. or less, most preferably 50° C. or less. The lower limit value of the temperature is usually 0° C. or more, preferably 10° C. or more.

The amount in which a solvent selected from the group consisting of nitrile and ketone is added or added dropwise is usually from 1 to 30 times, preferably from 2 to 25 times, more preferably from 3 to 10 times, the amount of the aqueous solution.

The time for which a solvent selected from the group consisting of nitrile and ketone is added or added dropwise is usually from 1 to 48 hours, preferably from 2 to 30 hours, most preferably from 3 to 20 hours.

After a crystal of a monovalent cation salt of HMB is thus precipitated, the precipitated crystal may be further ripened usually for 1 to 48 hours, preferably for 1 to 24 hours, most preferably for 1 to 12 hours. The "be ripened" means to grow the crystal by once stopping the step of precipitating a crystal of a monovalent cation salt of HMB.

After the ripening of crystal, the step of precipitating a crystal of a monovalent cation salt of HMB may be restarted. The process for collecting the crystal of a monovalent cation salt of HMB is not particularly limited but includes, for example, collection by filtration, pressurized filtration, suction filtration, centrifugal separation, and the like. Furthermore, in order to reduce attachment of the mother liquid and enhance the crystal quality, the crystal can be appropriately washed.

The solution used for washing the crystal is not particularly limited, but, for example, water, methanol, ethanol, acetone, n-propanol, isopropyl alcohol, acetonitrile, methyl ethyl ketone, methyl isobutyl ketone, diethyl ketone, or a solution prepared by mixing a plurality of kinds thereof in an arbitrary ratio, may be used.

The thus-obtained wet crystal is dried, whereby the crystal of the present invention can be obtained. As for the drying condition, reduced-pressure drying, vacuum drying, fluidized-bed drying, and forced air drying may be applied. The drying temperature may be any temperature as long as the attached water or solvent can be removed, but the temperature is preferably 80° C. or less, more preferably 60° C. or less.

Under the above-described crystallization conditions, a high-purity crystal of a monovalent cation salt of HMB can be obtained. The purity of the crystal of a monovalent cation salt of HMB is usually 95% or more, preferably 96% or more, more preferably 97% or more, most preferably 97.5% or more.

The crystal of a monovalent cation salt of HMB, which can be produced by the above-described production process, specifically includes, for example, a crystal of sodium HMB nonhydrate of which powder X-ray diffraction pattern using CuKα as the X-ray source is specified by the values shown in FIGS. 1 and 3 and Tables 1 and 3, a crystal of sodium HMB dihydrate specified by the values shown in FIG. 9 and Table 5, a crystal of potassium HMB nonhydrate specified by the values shown in FIG. 5 and Table 8, and a crystal of ammonium HMB nonhydrate specified by the values shown in FIG. 7 and Table 10.

[Analysis Examples]
(1) Powder X-Ray Diffraction

A powder X-ray diffraction apparatus (XRD), Ultima IV (manufactured by Rigaku Corporation), was used, and the measurement was performed according to the instruction book.

(2) Measurement of Concentration and Purity

The concentration and purity of HMB were measured using the following HPLC analysis conditions.

Guard column: Shodex SUGAR SH-G φ6.0×50 mm
Column: SUGAR SH1011 φ8.0×300 mm×2 columns in series
Column temperature: 60° C.
Buffer: 0.005 mol/L of an aqueous sulfuric acid solution
Flow velocity: 0.6 mL/min
Detector: UV detector (wavelength: 210 nm)

(3) Measurement of Water Content of Crystal by Karl-Fischer Method

An automatic water measurement apparatus, AQV-2200 (manufactured by Hiranuma Sangyo Co., Ltd.), was used, and the water content of the crystal was measured according to the instruction book.

(4) Measurement of Sodium Content and Potassium Content

An atomic absorption photometer, Z-2310 (manufactured by Hitachi High-Technologies Corporation), was used, and after dissolving the crystal of sodium HMB in 1 mol/L nitric acid, the concentration of sodium ion contained in the crystal was measured according to the instruction book.

(5) Measurement of Ammonium Content

The ammonium content was measured by a phthalaldehyde (OPA) method by using HPLC having a fluorescence detector.

(6) Measurement of Melting Point

Melting Point M-565 (manufactured by BÜCHI) was used, and the melting point was measured using the following conditions according to the instruction book.

60° C.-170° C., 1° C./min
30° C.-250° C., 2.5° C./min (Na-HMB dihydrate)

(7) Infrared Spectroscopic (IR) Analysis

Model FTIR-8400 (manufactured by Shimadzu Corporation) was used, and the analysis was performed according to the instruction book.

(8) Single Crystal X-Ray Structural Analysis

XtaLAB PRO (manufactured by Rigaku Corporation) was used, and the analysis was performed according to the instruction book.

Reference Example 1

Manufacture of Free HMB Solution

Reagent calcium HMB in an amount of 76.5 g in terms of the free form was dissolved in 850 mL of water. The obtained aqueous solution was passed through 640 mL of strong cation exchange resin, XUS-40232.01(H$^+$), to remove Ca and obtain 1.25 L of a solution containing 76.4 g of the free form.

EXAMPLES

Examples are described below, but the present invention is not limited to the following Examples.

Example 1

Acquisition of Crystal of Sodium HMB Nonhydrate (1)

To 200 mL of the aqueous free HMB solution obtained in Reference Example 1, 104 mL of an aqueous 1 mol/L sodium hydroxide solution was added to adjust the pH to 8.84. A 100 m L portion of the obtained aqueous solution was used for the next step.

100 mL of the aqueous solution was concentrated under reduced pressure at 50° C. and 10 mbar to remove the solvent, and a crystal of sodium HMB was thereby caused to naturally develop. The crystal slurry was further vacuum-dried to obtain 4.8 g of a crystal.

The results of powder X-ray diffraction of the crystal are shown in FIG. 1 and Table 1. The results of infrared spectroscopic analysis of the crystal are illustrated in FIG. 2. In the Table, "2θ" indicates the diffraction angle (2θ°), and "Relative Intensity" indicates the relative intensity ratio ($I/I_0$). The results when the relative intensity ratio was 1 or more are shown.

TABLE 1

| 2θ | Relative Intensity |
| --- | --- |
| 6.6 | 5 |
| 7.6 | 1 |
| 8.4 | 100 |
| 12.2 | 1 |
| 13.3 | 1 |
| 16.6 | 1 |
| 17.4 | 3 |

TABLE 1-continued

| 2θ | Relative Intensity |
|---|---|
| 17.8 | 1 |
| 18.0 | 1 |
| 18.9 | 1 |
| 19.7 | 2 |
| 21.1 | 2 |
| 22.5 | 1 |
| 23.1 | 1 |
| 23.9 | 3 |
| 24.6 | 2 |
| 25.4 | 3 |
| 26.9 | 1 |
| 28.8 | 1 |
| 29.4 | 1 |
| 29.9 | 1 |
| 30.6 | 1 |
| 30.9 | 1 |
| 32.2 | 1 |
| 34.0 | 1 |
| 34.4 | 1 |
| 35.1 | 2 |
| 38.2 | 1 |
| 41.4 | 1 |

The sodium content of the crystal was measured by the atomic absorption method and found to be 16.2 wt %, which substantially coincided with the theoretical value (16.4 wt %) of monosodium salt. In addition, the amount of water contained in the crystal was measured by the Karl-Fischer method and found to be 0.7 wt %. These results reveal that the crystal is a crystal of sodium HMB nonhydrate.

Various physical properties of the crystal acquired in Example 1 are shown in Table 2.

TABLE 2

| Water % | Sodium Content % | Melting Point ° C. |
|---|---|---|
| 0.7 | 16.2 | 105.0-110.0 |

Example 2

Acquisition of Crystal of Sodium HMB Nonhydrate (2)

To 200 mL of the aqueous free HMB solution obtained in Reference Example 1, 104 mL of an aqueous 1 mol/L sodium hydroxide solution was added to adjust the pH to 8.84. A 200 mL portion of the obtained aqueous solution was used for the next step.

200 mL of the aqueous solution was concentrated to 10 mL, and 50 mg of the crystal of sodium HMB obtained in Example 1 was added as a seed crystal. 20 mL of acetonitrile was added thereto to precipitate a crystal. The crystal slurry was stirred at room temperature for 1 hour, and the crystal was then collected by filtration, washed with 20 mL of acetonitrile, and vacuum-dried at 25° C. to obtain 6.7 g of a crystal.

The results of powder X-ray diffraction of the crystal are shown in FIG. 3 and Table 3. In the Table, "2θ" indicates the diffraction angle (2θ°), and "Relative Intensity" indicates the relative intensity ratio ($I/I_0$). The results when the relative intensity ratio was 1 or more are shown.

TABLE 3

| 2θ | Relative Intensity |
|---|---|
| 6.6 | 25 |
| 8.4 | 100 |

TABLE 3-continued

| 2θ | Relative Intensity |
|---|---|
| 12.2 | 2 |
| 13.3 | 4 |
| 16.6 | 3 |
| 17.3 | 4 |
| 17.8 | 3 |
| 18.0 | 3 |
| 18.8 | 3 |
| 19.7 | 4 |
| 21.0 | 2 |
| 22.5 | 2 |
| 23.1 | 2 |
| 23.9 | 3 |
| 24.5 | 3 |
| 25.3 | 3 |
| 29.4 | 4 |
| 29.9 | 3 |
| 30.9 | 2 |
| 32.2 | 3 |
| 35.1 | 4 |

The sodium content of the crystal was measured by the atomic absorption method and found to be 16.7 wt %, which substantially coincided with the theoretical value (16.4 wt %) of monosodium salt. In addition, the amount of water contained in the crystal was measured by the Karl-Fischer method and found to be 0.6 wt %. These results reveal that the crystal is a crystal of sodium HMB nonhydrate.

Various physical properties of the crystal acquired in Example 2 are shown in Table 4. As for pH, an aqueous solution of 100 g/L salt crystal in terms of free HMB was measured.

TABLE 4

| Water % | Sodium Content % | Melting Point ° C. | pH |
|---|---|---|---|
| 0.6 | 16.7 | 105.0-110.0 | 7.9 |

Example 3

Acquisition of Crystal of Sodium HMB Dihydrate

To 4.6 L of an aqueous solution containing 210.1 g of free HMB obtained according to the process of Reference Example 1, an aqueous 1 mol/L sodium hydroxide solution was added to adjust the pH to 7.92. The aqueous solution was concentrated to make 340.6 g of an aqueous solution, and 1 g of the crystal of sodium HMB obtained in Example 1 was added as a seed crystal at 35° C. to precipitate a crystal.

The crystal slurry was stirred at 30° C. for 16 hours and at 25° C. for 16 hours, and the crystal was then collected by filtration to obtain 130 g of a crystal. The crystal was further vacuum-dried (25° C., 20 hPa. 16 hours) to obtain 127 g of a crystal.

The results of powder X-ray diffraction of the crystal are shown in FIG. 9 and Table 5. The results of infrared spectroscopic analysis of the crystal are illustrated in FIG. 10. In the Table, "2θ" indicates the diffraction angle (2θ°), and "Relative Intensity" indicates the relative intensity ratio ($I/I_0$). The results when the relative intensity ratio was 1 or more are shown.

TABLE 5

| 2θ | Relative Intensity |
|---|---|
| 6.0 | 1 |
| 6.7 | 100 |
| 12.0 | 1 |
| 13.3 | 23 |
| 20.0 | 4 |
| 26.7 | 1 |
| 29.4 | 1 |
| 35.3 | 1 |
| 40.6 | 1 |
| 47.7 | 1 |

The sodium content of the crystal was measured by the atomic absorption method and found to be 16.4 wt %, which substantially coincided with the theoretical value (16.4 wt %) of monosodium salt. In addition, the amount of water contained in the crystal was measured by the Karl-Fischer method and found to be 19.5 wt %. These results reveal that the crystal is a crystal of sodium HMB dihydrate.

Various physical properties of the crystal acquired in Example 3 are shown in Table 6.

TABLE 6

| Water % | Sodium Content % | Melting Point °C. |
|---|---|---|
| 19.5 | 16.4 | 51 |

Example 4

Single Crystal X-Ray Structural Analysis

Single crystal X-ray diffraction (SXRD) was used for determining the structure of the crystal acquired in Example 3. The results thereof were summarized in Table 7. It was confirmed from the results that the crystal of sodium HMB is a dihydrate having water molecules in the unit lattice.

TABLE 7

| Chemical formula | Na$^+$•(C$_5$H$_9$O$_4$)$^-$•2H$_2$O |
|---|---|
| M$_w$ (g/mol) | 176.14 |
| Crystal Dimensions (mm) | 0.49 × 0.38 × 0.04 |
| Crystal System | monoclinic |
| Space Group | C2/c |
| a (Å) | 10.6679 (13) |
| b (Å) | 5.8862 (6) |
| c (Å) | 26.736 (4) |
| β (°) | 97.966 (13) |
| V (Å$^3$) | 1662.6 (4) |
| Z | 8 |
| D$_{calc}$ (g/cm$^3$) | 1.407 |
| T (° C.) | −180 |
| No. of reflections collected | 2951 |
| No. of independent reflections | 1494 |
| R$_{int}$ | 0.0267 |
| No. of variables | 117 |
| R (I > 2.0 σ(I))/R(all)$^a$ | 0.0631/0.0688 |
| wR2 (all)$^b$ | 0.1665 |
| Goodness of fit | 1.18 |
| Radiation (Å) | CuKα (λ = 1.54187 Å) |

$^a$R = Σ||F$_o$| − |F$_c$||/Σ|F$_o$|
$^b$wR2 = [Σ(w (F$_o^2$ − F$_c^2$)$^2$)/Σw(F$_o^2$)$^2$]$^{1/2}$, w = 1/[σ$^2$(F$_o^2$) + (0.1011P)$^2$]

Example 5

Acquisition of Crystal of Potassium HMB Nonhydrate

To 200 mL of the aqueous free HMB solution obtained in Reference Example 1, 114 mL of an aqueous 1 mol/L potassium hydroxide solution was added to adjust the pH to 8.85. 314 mL of the aqueous solution was concentrated under reduced pressure at 50° C. and 10 mbar to remove the solvent, and a crystal of potassium HMB was thereby caused to naturally develop. The crystal slurry was further vacuum-dried to obtain 14.8 g of a crystal.

The results of powder X-ray diffraction of the crystal are shown in FIG. 5 and Table 8. The results of infrared spectroscopic analysis of the crystal are illustrated in FIG. 6. In the Table, "2θ" indicates the diffraction angle (2θ°), and "Relative Intensity" indicates the relative intensity ratio (I/I$_0$). The results when the relative intensity ratio was 1 or more are shown.

TABLE 8

| 2θ | Relative Intensity |
|---|---|
| 6.4 | 1 |
| 8.1 | 1 |
| 9.0 | 100 |
| 16.1 | 2 |
| 18.7 | 1 |
| 22.9 | 2 |
| 23.8 | 4 |
| 24.6 | 1 |
| 27.1 | 4 |
| 28.5 | 1 |
| 29.4 | 1 |
| 30.7 | 2 |
| 31.1 | 1 |
| 32.1 | 1 |
| 33.8 | 1 |
| 34.4 | 1 |
| 35.0 | 1 |
| 39.6 | 1 |
| 40.1 | 1 |

The potassium content of the crystal was measured by the atomic absorption method and found to be 24.3 wt %, which substantially coincided with the theoretical value (25.0 wt %) of monopotassium salt. In addition, the amount of water contained in the crystal was measured by the Karl-Fischer method and found to be 0.6 wt %. These results reveal that the crystal is a crystal of potassium HMB nonhydrate.

Various physical properties of the crystal acquired in Example 5 are shown in Table 9. As for pH, an aqueous solution of 100 g/L salt crystal in terms of free HMB was measured.

TABLE 9

| Water % | Potassium Content % | Melting Point °C. | pH |
|---|---|---|---|
| 0.6 | 24.3 | 154.3-157.4 | 7.9 |

Example 6

Acquisition of Seed Crystal of Ammonium HMB Nonhydrate (1)

To 20 mL of the aqueous free HMB solution obtained in Reference Example 1, 8.5 mL of an aqueous 1.4 M ammonium solution was added to adjust the pH to 7.90. 28.5 mL of the aqueous solution was concentrated to make 1.6 mL and after adding 5 mL of acetonitrile, the aqueous solution was left standing still at room temperature for 30 minutes to precipitate a crystal. The crystal slurry was further stirred at room temperature for 1 hour, and the crystal was then collected by filtration to obtain 0.4 g of a seed crystal.

Example 7

Acquisition of Crystal of Ammonium HMB Nonhydrate (2)

To 200 mL of the aqueous free HMB solution obtained in Reference Example 1, 64 mL of an aqueous 1.4 M ammonium solution was added to adjust the pH to 7.75.

246 mL of the aqueous solution obtained above was concentrated to make 10.5 mL, and 15 mg of the crystal of ammonium HMB obtained in Example 4 was added as a seed crystal. Thereto, 15 mL of acetonitrile was added to precipitate a crystal. The crystal slurry was stirred at room temperature for 1 hour, and the crystal was then collected by filtration, washed with 50 mL of acetonitrile, and vacuum-dried at 25° C. to obtain 4.7 g of a crystal.

The results of powder X-ray diffraction of the crystal are shown in FIG. 7 and Table 10. The results of infrared spectroscopic analysis of the crystal are illustrated in FIG. 8. In the Table, "2θ" indicates the diffraction angle (2θ°), and "Relative Intensity" indicates the relative intensity ratio ($I/I_0$). The results when the relative intensity ratio was 1 or more are shown.

TABLE 10

| 2θ | Relative Intensity |
| --- | --- |
| 7.5 | 1 |
| 8.6 | 1 |
| 10.0 | 1 |
| 12.8 | 1 |
| 14.3 | 1 |
| 15.5 | 1 |
| 16.1 | 1 |
| 17.3 | 2 |
| 18.0 | 2 |
| 18.2 | 1 |
| 18.6 | 1 |
| 19.9 | 100 |
| 21.1 | 4 |
| 21.9 | 1 |
| 22.6 | 1 |
| 25.1 | 1 |
| 25.6 | 1 |
| 26.1 | 1 |
| 27.4 | 1 |
| 28.8 | 1 |
| 29.9 | 3 |
| 31.2 | 1 |
| 34.4 | 1 |
| 37.4 | 1 |
| 38.0 | 1 |
| 39.6 | 1 |
| 39.7 | 1 |
| 40.5 | 1 |
| 40.6 | 1 |
| 42.2 | 1 |
| 43.2 | 1 |

The ammonium content of the crystal was measured by HPLC and found to be 13.2 wt %, which substantially coincided with the theoretical value (13.3 wt %) of monoammonium salt. In addition, the amount of water contained in the crystal was measured by the Karl-Fischer method and found to be 0.5 wt %. These results reveal that the crystal is a crystal of ammonium HMB nonhydrate.

Various physical properties of the crystal acquired in Example 7 are shown in Table 11. As for pH, an aqueous solution of 100 g/L salt crystal in terms of free HMB was measured.

TABLE 11

| Water % | Ammonium Content % | Melting Point ° C. | pH |
| --- | --- | --- | --- |
| 0.5 | 13.2 | 138.0-143.1 | 5.7 |

Example 8

Measurement of Solubility

The crystal of monovalent cation salt nonhydrate of HMB, obtained in each of Examples 2, 5 and 7, was added at room temperature until it dissolved in water and after keeping the solution for a sufficient time under stirring, the supernatant containing no crystal was sampled and measured for the HMB concentration by using HPLC. The measurement results are shown in Table 12.

TABLE 12

| | Solubility (g/L) | Solubility (in terms of free form) (g/L) |
| --- | --- | --- |
| Sodium HMB nonhydrate | 729 | 513 |
| Potassium HMB nonhydrate | 1011 | 764 |
| Ammonium HMB nonhydrate | 660 | 577 |
| Calcium HMB hydrate (*1) | 150 | 129 |

(*1): Purchased from Tokyo Chemical Industry Co., Ltd.

As shown in Table 12, it is understood that the acquired crystals of sodium HMB nonhydrate, potassium HMB nonhydrate and ammonium HMB nonhydrate are greatly enhanced in the solubility in water, as compared to an existing calcium salt.

Example 9

Mixing of Crystal of Monovalent Cation Salt of HMB and Phosphate Buffer

A 100 g/L solution, in terms of free form, was prepared using the crystal of monovalent cation salt nonhydrate of HMB, obtained in each of Examples 2, 5 and 7, and mixed with 0.2 M phosphate buffer (pH: 6.80) in an arbitrary mixing ratio. The solution after mixing was measured for the light transmittance (660 nm) to evaluate the presence or absence of insoluble salt formation. The results are shown in Table 13. In Table 13, "-" indicates unevaluated.

TABLE 13

| | Transmittance T % (660 nm) | | | |
| --- | --- | --- | --- | --- |
| | Mixing Ratio (Vol/Vol) (*1) | | | |
| | 0.01 | 0.17 | 0.33 | 0.57 |
| Sodium salt | — | 100 | 100 | 100 |
| Potassium salt | — | 100 | 100 | 100 |
| Ammonium salt | — | 100 | 100 | 100 |
| Calcium salt | 60 | 0.11 | 0.02 | 0 |

(*1) Vol/Vol = aqueous 100 g/L HMB solution (Vol)/0.2M phosphate buffer (Vol)

As shown in Table 13, it is understood that in the mixing with phosphate buffer, the existing calcium salt produces an insoluble salt but the acquired crystals of sodium HMB nonhydrate, potassium HMB nonhydrate and ammonium HMB nonhydrate do not form an insoluble salt.

Example 10

Mixing of Crystal of Sodium HMB and Glucose-Amino Acids-Electrolytes Infusion Solution The sodium HMB nonhydrate obtained in Example 2 was mixed with a glucose-amino acids-electrolytes infusion solution for peripheral vain nutrition [pH: about 6.7; Product Name: Aminofluid Infusion Solution (Otsuka Pharmaceutical Factory, Inc.)] to obtain 0, 0.11, 0.21 and 0.42 weight/volume % solutions at final concentration in terms of free form. The light transmittance (660 nm) was measured by ultraviolet and visible spectrophotometer immediately after the mixing or 24 hours after being left at room temperature to evaluate the presence or absence of insoluble salt formation. The results are shown in Table 14.

TABLE 14

Transmittance T % (660 nm)

| HMB final concentration (weight/Volume %) | T (%) Time after addition (h) | | | |
|---|---|---|---|---|
| | 0 | 24 | 0 | 24 |
| | calcium salt | | sodium salt | |
| 0 | 100 | 100 | 100 | 100 |
| 0.11 | 100 | 70 | 100 | 100 |
| 0.21 | 90 | 28 | 100 | 100 |
| 0.42 | 65 | 20 | 100 | 100 |

As shown in Table 14, it is understood that in the mixing with the Aminofluid infusion solution, the existing calcium salt forms an insoluble salt but the sodium HMB nonhydrate does not form an insoluble salt.

Example 11

Effect on Body Electrolyte when Glucose-Electrolytes Infusion Solution Containing Crystal of Sodium HMB is Administered The sodium HMB nonhydrate obtained in Example 2 was mixed with a glucose-electrolytes infusion solution that does not contain phosphate ion [Product Name: SOLITA-T No. 3 Infusion Solution (AY Pharmaceuticals Co., Ltd.)] to obtain 0 and 0.42 weight/volume % solutions at final concentration in terms of free form. The solution was continuously administered to a rat on which operative stress was incurred by intestinal tract scratch operation at a normal dose (240 mL/kg/day) for 3 days. On the final day of administration, urine was collected by 24-hour urine collection and measured for the urinary electrolyte concentration. The results are shown in Tables 15 and 16.

TABLE 15

Urinary calcium excretion amount (mg/day)

| HMB final concentration (weight/volume %) | Urinary calcium excretion amount (mg/day) | |
|---|---|---|
| | calcium salt | sodium salt |
| 0 | 0.30 | 0.30 |
| 0.42 | 3.64 | 0.25 |

TABLE 16

Urinary phosphate excretion amount (mg/day)

| HMB final concentration (weight/volume %) | Urinary phosphate excretion amount (mg/day) | |
|---|---|---|
| | calcium salt | sodium salt |
| 0 | 18.4 | 18.4 |
| 0.42 | 4.4 | 19.2 |

As shown in Tables 15 and 16, it is understood that in the administration of a mixture with the SOLITA-T No. 3 infusion solution, the existing calcium salt induces the increase in urinary calcium and the decrease in urinary phosphate excretion but the acquired crystal of sodium HMB nonhydrate does not induce the above electrolyte abnormality.

While the invention has been described in detail and with reference to specific embodiments thereof, it will be apparent to one skilled in the art that various changes and modifications can be made therein without departing from the spirit and scope of the invention. This application is based on Japanese Patent Application (Patent Application No. 2015-226876) filed on Nov. 19, 2015, and Japanese Patent Application (Patent Application No. 2016-108805) filed on May 31, 2016, the entirety of which is incorporated herein by way of reference. All references cited herein are incorporated herein in their entirety.

INDUSTRIAL APPLICABILITY

According to the present invention, a crystal of a monovalent cation salt of HMB, which is useful, for example, as a product, a raw material, an intermediate or the like of health food, medicines, cosmetics, or the like, and a production process thereof are provided.

The invention claimed is:

1. A crystal of a monovalent cation salt of 3-hydroxyisovaleric acid, wherein the monovalent cation salt is a sodium salt having a powder X-ray diffraction with crystal peaks at diffraction angles (2θ) of 8.4±0.2°, 6.6±0.2°, 19.7±0.2°, 13.3±0.2°, and 29.4±0.2°;
   the monovalent cation salt is a sodium salt having a powder X-ray diffraction with crystal peaks at diffraction angles (2θ) of 6.7±0.2°, 13.3±0.2°, and 20.0±0.2°;
   the monovalent cation salt is a potassium salt having a powder X-ray diffraction with crystal peaks at diffraction angles (2θ) of 9.0±0.2°, 27.1±0.2°, 23.8±0.2°, 16.1±0.2°, and 22.9±0.2°; or
   the monovalent cation salt is an ammonium salt having a powder X-ray diffraction with crystal peaks at diffraction angles (2θ) of 19.9±0.2°, 21.1±0.2°, 29.9±0.2°, 17.3±0.2°, and 18.0±0.2°.

2. The crystal according to claim 1, wherein the monovalent cation salt is a sodium salt having a powder X-ray diffraction with crystal peaks at diffraction angles (2θ) of 8.4±0.2°, 6.6±0.2°, 19.7±0.2°, 13.3±0.2°, and 29.4±0.2°.

3. The crystal according to claim 2, wherein the crystal further has peaks at diffraction angles (2θ) of 35.1±0.2°, 17.3±0.2°, 24.5±0.2°, 17.8±0.2°, and 29.9±0.2°.

4. The crystal according to claim 3, wherein the crystal further has peaks at diffraction angles (2θ) of 16.6±0.2°, 23.9±0.2°, 18.8±0.2°, 18.0±0.2°, and 25.3±0.2°.

5. The crystal according to claim 1, wherein the monovalent cation salt is a sodium salt having a powder X-ray diffraction with crystal peaks at diffraction angles (2θ) of 6.7±0.2°, 13.3±0.2°, and 20.0±0.2°.

6. The crystal according to claim 5, wherein the crystal further has peaks at diffraction angles (2θ) of 6.0±0.2°, 47.7±0.2°, 40.6±0.2°, 26.7±0.2°, and 12.0±0.2°.

7. The crystal according to claim 5, wherein the crystal has approximately the following unit cell parameters when measured at about −180° C.: a=10.6679 Å; b=5.8862 Å; c=26.736 Å; α=90°; β=97.966°; γ=90°; V=1662.6 Å3; and Z=8; the calculated density ($D_{calc}$, gcm$^{-3}$) is 1.407 gcm$^{-3}$; and the space group is C2/c.

8. The crystal according to claim 1, wherein the monovalent cation salt is a potassium salt having a powder X-ray diffraction with crystal peaks at diffraction angles (2θ) of 9.0±0.2°, 27.1±0.2°, 23.8±0.2°, 16.1±0.2°, and 22.9±0.2°.

9. The crystal according to claim 8, wherein the crystal further has peaks at diffraction angles (2θ) of 30.7±0.2°, 8.1±0.2°, 6.4±0.2°, 32.1±0.2°, and 28.5±0.2°.

10. The crystal according to claim 9, wherein the crystal further has peaks at diffraction angles (2θ) of 40.1±0.2°, 31.1±0.2°, 24.6±0.2°, 18.7±0.2°, and 34.4±0.2°.

11. The crystal according to claim 1, wherein the monovalent cation salt is an ammonium salt having a powder X-ray diffraction with crystal peaks at diffraction angles (2θ) of 19.9±0.2°, 21.1±0.2°, 29.9±0.2°, 17.3±0.2°, and 18.0±0.2°.

12. The crystal according to claim 11, wherein the crystal further has peaks at diffraction angles (2θ) of 25.6±0.2°, 8.6±0.2°, 18.2±0.2°, 39.6±0.2°, and 40.5±0.2°.

13. The crystal according to claim 12, wherein the crystal further has peaks at diffraction angles (2θ) of 28.8±0.2°, 39.7±0.2°, 18.6±0.2°, 15.5±0.2°, and 14.3±0.2°.

14. A process for producing a crystal of a monovalent cation salt of 3-hydroxyisovaleric acid (HMB) of claim 1, comprising a step of concentrating an aqueous HMB solution containing a monovalent cation-containing compound and having a pH of 4.0 to 10.0 under reduced pressure at 20 to 60° C. to precipitate a crystal of a monovalent cation salt of HMB in the aqueous solution, and a step of collecting the crystal of a monovalent cation salt of HMB from the aqueous solution, wherein the monovalent cation-containing compound is a sodium-containing compound, a potassium-containing compound, or an ammonium-containing compound.

15. A process for producing a crystal of a monovalent cation salt of 3-hydroxyisovaleric acid (HMB) of claim 1, comprising a step of adding, as a seed crystal, a crystal of a monovalent cation salt of HMB to an aqueous HMB solution containing a monovalent cation-containing compound and having a pH of 4.0 to 10.0, a step of precipitating a crystal of a monovalent cation salt of HMB in the aqueous solution, and a step of collecting the crystal of a monovalent cation salt of HMB from the aqueous solution, wherein the monovalent cation-containing compound is a sodium-containing compound, a potassium-containing compound, or an ammonium-containing compound.

16. The process according to claim 15, wherein the step of precipitating a monovalent cation salt of HMB is a step of adding or adding dropwise a solvent selected from the group consisting of nitrile and ketone to precipitate a crystal of a monovalent cation salt of HMB.

17. The process according to claim 16, wherein the nitrile is acetonitrile and the ketone is a solvent selected from the group consisting of acetone, methyl ethyl ketone, methyl isobutyl ketone and diethyl ketone.

18. The process according to claim 11, wherein the monovalent cation-containing compound is a sodium-containing compound.

19. The process according to claim 11, wherein the monovalent cation-containing compound is a potassium-containing compound.

20. The process according to claim 11, wherein the monovalent cation-containing compound is an ammonium-containing compound.

21. The process according to claim 15, wherein the monovalent cation-containing compound is a sodium-containing compound.

22. The process according to claim 15, wherein the monovalent cation-containing compound is a potassium-cotaming compound.

23. The process according to claim 15, wherein the monovalent cation-containing compound is an ammonium-containing compound.

* * * * *

UNITED STATES PATENT AND TRADEMARK OFFICE
CERTIFICATE OF CORRECTION

PATENT NO. : 10,647,653 B2
APPLICATION NO. : 15/777318
DATED : May 12, 2020
INVENTOR(S) : Yokoi et al.

Page 1 of 1

It is certified that error appears in the above-identified patent and that said Letters Patent is hereby corrected as shown below:

In the Claims

Claim 22, Column 20, Lines 37-38, "potassium-cotaming" should read "potassium-containing"

Signed and Sealed this
First Day of September, 2020

Andrei Iancu
*Director of the United States Patent and Trademark Office*